US009580760B2

(12) United States Patent
Oppedahl et al.

(10) Patent No.: US 9,580,760 B2
(45) Date of Patent: Feb. 28, 2017

(54) RAPID DETECTION OF MOLD BY ACCELERATED GROWTH AND DETECTION

(75) Inventors: Angela M. Oppedahl, Boone, IA (US); Steven J. Lasky, Ankeny, IA (US); Dylan D. Baker, West Des Moines, IA (US); Daniel Buttry, Laramie, WY (US); Ann M. Steger, Des Moines, IA (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 1053 days.

(21) Appl. No.: 11/729,120

(22) Filed: Mar. 28, 2007

(65) Prior Publication Data

US 2007/0231852 A1 Oct. 4, 2007

Related U.S. Application Data

(60) Provisional application No. 60/786,498, filed on Mar. 28, 2006.

(51) Int. Cl.
*C12N 1/14* (2006.01)
*C12Q 1/68* (2006.01)
*C12N 1/38* (2006.01)
*C12Q 1/04* (2006.01)

(52) U.S. Cl.
CPC ............ *C12Q 1/6895* (2013.01); *C12N 1/14* (2013.01); *C12N 1/38* (2013.01); *C12Q 1/04* (2013.01); *C12Q 1/045* (2013.01)

(58) Field of Classification Search
None
See application file for complete search history.

(56) References Cited

U.S. PATENT DOCUMENTS

| | | | | |
|---|---|---|---|---|
| 4,014,748 A * | 3/1977 | Spinner et al. | ............... | 600/572 |
| 5,031,635 A * | 7/1991 | Koll | ............... | 600/569 |
| 5,091,316 A * | 2/1992 | Monthony et al. | ........... | 600/572 |
| 6,323,337 B1 * | 11/2001 | Singer et al. | ................ | 536/26.6 |
| 6,473,171 B1 | 10/2002 | Buttry et al. | | |
| 6,602,675 B2 * | 8/2003 | Short et al. | ................... | 435/7.32 |
| 7,205,100 B2 * | 4/2007 | Buttry et al. | ..................... | 435/4 |
| 7,291,465 B2 * | 11/2007 | Karaolis | ...................... | 435/6.13 |
| 2005/0048509 A1 * | 3/2005 | Han et al. | ........................ | 435/6 |

FOREIGN PATENT DOCUMENTS

EP 1118676 * 7/2001 ............... C12Q 1/24

OTHER PUBLICATIONS

Hutter et al., "Flow Cytometric Determination of cellular Substances in Algae, Bacteria, Moulds, and Yeasts", Antonie van Ieeuwenhoek, 1978, vol. 44, pp. 269-282.*
Munroe, S., How to Detect Mildew in Vents, SFGATE, Home Guides, http://homeguides.sfgate.com/detect-mildew-vents-31998. html, accessed on Jan. 8, 2014.*
Infection and Immunity, Jun. 2000, p. 3377-3384, vol. 68, No. 6 "Adhesion of *Aspergillus* Species to Extracellular Matrix Proteins: Evidence for Involvement of Negatively Charged Carbohydrates on the Conidial Surface," by Julie A. Wasylnkal and Margo M. Moore.
"Involvement of Secreted Aspergillus Fumigatus Proteases in Disruption of the Actin Fiber Cytoskeleton and Loss of Focal Adhesion Sites in Infected A549 Lung Pneumocytes," by Tanya V. Kogan, Jeries Jadoun, Leonid Mittelman, Koret Hirschberg, and Nir Osherov, The Journal of Infectious Diseases, vol. 187 (2004), pp. 1965-1973.
USDA Bacteriological Analytical Manual Online Chapter 23, Microbiological Methods for Cosmetics, Aug. 2001, entire publication, also at www.cfsan.fda.gove/~ebarn/bar-23.html.
Davey et al, "Variable Selection and Multivariate Methods for the Identification of Microorganisms by Flow Cytometry," (Cytometry), 1999, vol. 35, pp. 162-168.
Office Action for U.S. Appl. No. 12/103,282, 8 pages, dated Apr. 6, 2009.
Amendment for U.S. Appl. No. 12/103,282, 8 pages, filed Aug. 6, 2009.

* cited by examiner

*Primary Examiner* — Louise W Humphrey
*Assistant Examiner* — Christopher Keller
(74) *Attorney, Agent, or Firm* — Knobbe, Martens, Olson & Bear, LLP

(57) ABSTRACT

The invention includes a method of detecting the presence or absence of mold in a sample. The method can include the step of applying a sample suspected of containing the mold to a growth medium, optionally fragmenting the sample, associating the sample with a labeling agent, and detecting the presence or absence of the mold by detection of the labeling agent. The invention can also include a medium for growing mold that includes a stimulation agent.

8 Claims, 1 Drawing Sheet

RAPID DETECTION OF MOLD BY ACCELERATED GROWTH AND DETECTION

RELATED APPLICATIONS

This application claims the benefit of U.S. Provisional Patent Application Ser. No. 60/786,498, titled Rapid Detection of Mold by Accelerated Growth and Detection, filed Mar. 28, 2006, the contents of which are hereby incorporated by reference.

FIELD OF THE INVENTION

The invention generally relates to the detection of mold in a sample.

BACKGROUND OF THE INVENTION

For many products, determining if the product contains mold is an important consideration before the product is placed on the market. Such considerations are particularly important for products intended to be used on or in a mammalian body. Unfortunately, many current methods of testing for the presence of mold take several days to complete. More specifically, a traditional plate count test typically takes about five to seven days before it can be determined if the product contains mold. Such a delay causes the product to consume a portion of its shelf life, even if the product ultimately passes the mold test.

SUMMARY OF THE INVENTION

In some embodiments, the invention includes a method of detecting the presence or absence of mold in a sample. The method can include the step of applying a sample suspected of containing the mold to a growth medium. After the sample is exposed to the growth medium for a sufficient duration to grow the mold, the sample can optionally be fragmented. After fragmentation, the sample can be associated with a labeling agent, and the presence or absence of the mold in the sample can be determined by detecting the fragments that are associated with the labeling agent. Such embodiments of the invention accelerate the growth of any mold in the sample, and significantly reduce the time to detection compared to traditional tests. For example, in some embodiments of the invention, the presence or absence of mold in a sample can be determined in less than about twenty-four hours.

In some embodiments, the invention includes a medium for growing mold. The growth medium can include a nitrogenous substance, a sample neutralization agent, a carbohydrate source, a carbon source, and a stimulation agent. The stimulation agent can be provided to stimulate the growth of any mold present in the sample while it is in the presence of the growth medium. Such a stimulation agent contributes to the reduction of the time required before the mold can be detected.

In some embodiments, the invention includes a method for detecting the presence or absence of mold in a sample. Such embodiments may include the steps of applying a sample suspected of containing the mold to a growth medium having a substrate useful for supporting mold growth, associating the sample with a labeling agent, the labeling agent including a fluorescent agent, and detecting the presence or absence of mold in the sample by placing the substrate into a fluorescence chamber, the presence of mold being detectable by the labeling agent associated with the mold.

DETAILED DESCRIPTION OF THE INVENTION

Figure 1:
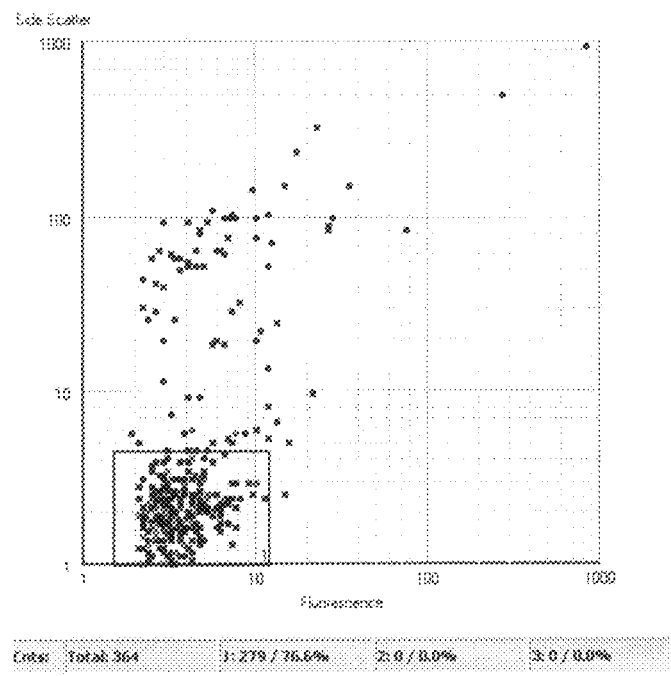
FIG. 1 shows a scatter plot of mold hyphae stained with a fluorochrome in a growth medium in accordance with an embodiment of the invention.

For the purpose of promoting an understanding of the principles of the invention, reference will now be made to the embodiments illustrated in the drawings and specific language will be used to describe the same. It will, nevertheless, be understood that no limitation of the scope of the invention is thereby intended; any alterations and further modifications of the described or illustrated embodiments, and any further applications of the principles of the invention as illustrated therein, are contemplated as would normally occur to one skilled in the art to which the invention relates.

Embodiments of the invention relate to a method of detecting mold in a sample. In some embodiments, the method includes the steps of preparing the sample, applying the sample to a growth medium, growing the sample on or in the presence of the growth medium, fragmenting the sample, associating the sample with a labeling agent, and detecting the presence or absence of mold in the sample. Such a method is useful for rapidly detecting the presence or absence of mold in a sample. In some embodiments, the presence or absence of the mold can be detected within about 20 to about 24 hours of applying the sample to the growth medium. The shorter portion of the range (e.g., about 20 to about 22 hours) corresponds to a more heavily contaminated sample, while the longer portion of the range (e.g., about 22 to about 24 hours) corresponds to a lesser contaminated sample. However, substantially all samples can be analyzed to determine if they contain mold in less than about 24 hours. This relatively short period of time is in contrast to known mold detection methods, which generally take several days before the presence or absence of mold is determined.

Any sample can be analyzed to determine if mold is present or absent in accordance with embodiments of the invention. For example, samples of commercial products (e.g., over-the-counter products) can be tested to determine if they contain mold before they are placed in commerce. Examples of such commercial products include products designed or intended for application or use on or in a mammalian body. In some embodiments, the sample can include a personal care product (PCP); for example, make-up (such as eye shadow, blush, mascara or the like); over-the-counter medications (such as nasal spray, vitamins, aspirin or the like); beauty products (such as shampoo, lotion, shaving gels/creams) or any product that may be used as a personal care item. In some embodiments, the invention relates to a method for preparing PCP samples for a compendial methods test.

Accordingly, methods in accordance with embodiments of the invention are useful for allowing a sample of a commercial product to be tested for the presence or absence of mold and providing a rapid determination of whether mold is present in the sample. Such a rapid determination is useful, for example, because it allows the batch of the commercial product from which the sample was taken to be released into the market if the sample passes the mold test or, in the alternative, disposed of or treated if the sample fails the mold test. Such a determination can be made in a relatively quick manner that avoids the need for storing the batch of commercial product for long periods of time. Embodiments of methods of the invention are useful for detecting any type of mold. For example, mold detectable by the sample includes *Aspergillus* species, *Penicillium* species, and the like.

The sample can be prepared by any suitable method. In some embodiments, the sample can be directly taken from a batch of a commercial product. The sample size of the product should be sufficient to provide an adequate sample and not to be influenced by the sampling procedure. In some embodiments, the sample of the commercial product is subjected to one or more preparation steps before it is applied to a growth medium. For example, any anti-microbial agents present in the sample can be neutralized so that it does not interfere with the growth of any mold present in the sample. In certain embodiments, the sample preparation includes a dilution step where about 10 grams of the product is placed in about 90 mL of a media (such as those indicated in applicable compendial guidelines). After dilution, the sample can be placed in a growth enhancement medium.

The growth medium can include any media useful for growing any mold present in the sample. In some embodiments, the growth medium is useful for facilitating the rapid growth of any mold present in the sample, easy to fragment in accordance with embodiments of the invention, as discussed further below, and/or does not interfere with the mold detection step of embodiments of the invention, as described further below. In some embodiments, the growth medium is useful for stimulating mold growth and producing mold hyphae.

For example, the growth medium may comprise a nitrogenous substance useful for promoting fungal growth, such as Tryptic Soy Broth (e.g., at a concentration of about 5 g/L to about 30 g/L (e.g., about 30 g/L)); a sample neutralization agent, such as soy lecithin (e.g., at a concentration of about 5 g/L to about 50 g/L (e.g., about 5 g/L)) and/or Tween-20 (e.g., at a concentration of about 40 mL/L to about 100 mL/L (e.g., about 40 mL/L)); a substance high in carbohydrate content, such as malt extract (e.g., at a concentration of about 5 g/L to about 20 g/L (e.g., about 10 g/L)); and/or a carbon source, such as dextrose (e.g., at a concentration of about 2 g/L to about 20 g/L (e.g., about 10 g/L)).

In some embodiments, the growth medium includes a stimulation agent to stimulate growth of the hyphal strands. In certain embodiments, the stimulation agent is n-acetyl glucosamine. N-acetyl glucosamine (NAG) is a naturally occurring amino sugar that is a primary component of chitin, the fibrous structure of the fungal cell wall. The n-acetyl glucosamine can be included at any concentration suitable to stimulate the growth of the hyphal strands. For example, the n-acetyl glucosamine can be present at a concentration range of about 5 mM to about 450 mM (e.g., about 50 mM to about 100 mM, such as about 75 mM). In certain embodiments, the growth medium is a liquid (sometimes referred to as a broth).

In some embodiments, the growth medium is made as follows: The nitrogenous substance useful for fungal growth, the sample neutralization agent, the substance high in carbohydrate content, and/or the carbon source can be measured and/or weighed and placed in about 1L of deionized water. This solution can be mixed with a magnetic stir bar while heated to a boiling temperature to dissolve the ingredients. The solution can then be autoclaved at about 121° C. for about 15 minutes, cooled to room temperature and the growth stimulation agent can be weighed and added to the mixture while stirring. The broth pH can then be measured and adjusted to 7.0±0.2. The entire solution can then be sterile filtered through a 0.2 um filter. In certain embodiments, each component could be measured and/or weighed, boiled to dissolve, pH adjusted, sterile filtered and/or autoclaved for sterility. The growth medium can be stored at a storage temperature of about 4° C.±2° C., and should be stable for at least about 6 months.

In some embodiments, the growth medium can include one or more solid articles (including but not limited to substrates, such as, swabs, mesh-like devices attached to a shaft, sponges, and/or free-standing meshes or screens, and/or fragmentation enhancers, such as small bead-like objects, metallic beads, ceramic beads, chips of ceramic materials, magnets, and the like). The solid articles can provide a place for mold to attach and grow, and/or can be useful for fragmenting mold, as described further below.

In some embodiments, a solid article comprising a substrate can be utilized to concentrate and isolate the mold from the product matrix and other debris in the sample. The substrate can be placed on or in the growth medium and, in some embodiments, can be removed after mold growth is promoted (e.g., less than or about 24 hours). In certain embodiments, the substrate is porous and supports growth of the mold onto its porous surface.

In certain embodiments, one or more surfaces of the solid article (e.g., substrate) are derivatized to promote mold adhesion. For example, the adhesion of the mold to the solid additive or substrate can be promoted by coating the solid article with a negatively charged surface group to promote adhesion through interaction of surface functional groups on the mold, such as the negatively charged proteins of the type described in Infection and Immunity, June 2000, p. 3377-3384, Vol. 68, No. 6 "Adhesion of Aspergillus Species to Extracellular Matrix Proteins: Evidence for Involvement of Negatively Charged Carbohydrates on the Conidial Surface," by Julie A. Wasylnkal and Margo M. Moore, the relevant contents of which are hereby incorporated by reference. As another example, one or more of the surfaces of the solid article can be coated with a actin-containing structure. This approach takes advantage of the fact that mold may contain enzymes that may disrupt the actin cytoskeleton of certain cells, thereby producing enhanced adhesion to such cells. This action of the mold and mold enzymes is described in "Involvement of Secreted Aspergillus fumigatus Proteases in Disruption of the Actin Fiber Cytoskeleton and Loss of Focal Adhesion Sites in Infected A549 Lung Pneumocytes," by Tanya V. Kogan, Jeries Jadoun, Leonid Mittelman, Koret Hirschberg, and Nir Osherov, The Journal of Infectious Diseases, volume 189 (2004), pages 1965-1973, the relevant contents of which is hereby incorporated by reference. In other embodiments, immunoglobulin G, antibodies targeting *A. niger*, concanavilin A and fibronectin can be applied to the substrate surface to derivatize it.

The optimal type of surface derivatization and the way of achieving it depends on the type of substrate used. For example, in embodiments of the substrate that comprise metal screens or meshes, polymeric screens or meshes, glass surfaces (both rough and smooth), and polymer surfaces (both rough and smooth), suitable surface derivatizing agents include various polymers that can be dip or spray coated onto the surface, reagents that can be used to covalently bond functional groups onto the surface (such as silanes for glass surfaces), and/or chemical treatments that introduce functional groups directly onto the surface (such as chemical oxidation of polyethylene with chromic acid to produce interfacial carboxylic acid groups that can then be deprotonated to give carboxylates). Introducing negative charges to promote mold adhesion can be achieved by derivatizing the substrate surface with agents that bear negative charges, such as $-SO_3^-$ (sulfonate) groups, $-CO_2^-$ (carboxylate) groups, $-PO_3^{2-}$ (phosphonate groups), and the like.

In embodiments in which the substrate surface is derivatized with polymers, the polymers can be dip or spray coated onto the substrate surface. Such polymers include, for example, polystyrene sulfonate, which has $-SO_3^-$ (sulfonate) groups; polyacrylic acid, which has pendant $-CO_2^-$ (carboxylate) groups, polymeric phosphonates and the like. Copolymers that contain pendant anionic groups can also be utilized. For example, partially carboxylated polyacrylamide can be utilized. In some embodiments, these polymers can be crosslinked to protect them against dissolution in water. Such crosslinking can be achieved by adding cross-linking agents that crosslink under ultraviolet-visible irradiation or gamma irradiation.

Polymeric substrates can also be oxidized using an oxidizing agent, including chromic acid, persulfate, and the like. Oxidation can be done on a wide variety of polymers, including relatively less reactive polymers such as polyethylene and relatively more reactive polymers such as nylon, rayon and polyurethane.

Also, adhesion of the polymer to the surface can be promoted by use of polymers containing plasticizers, such as polyvinyl chloride plasticized by dioctyl phthalate or dioctyl adipate. Plasticizers can increase adhesion of the deteriogenic fungus *Aureobasidium pullulans* to polyvinyl chloride.

In embodiments including glass substrates, mono-, di-, or tri-methoxy silanes (which provide attachment to glass surfaces) that bear sulfonate, carboxylate or phosphonate groups can be utilized to derivatize the surface. In some embodiments, the methoxy group(s) can be substituted with ethoxy or chloro groups, which also provide for attachment to glass.

Another approach to promote mold adhesion to the substrate is to introduce surface coatings that mold can use enzymatic processes to adhere to. The coating can include any material to which mold is known to adhere, such as, for example, cellulose and its derivatives (often used as thickeners), actin (G-actin), polymeric forms of actin (such as F-actin), chitin, polymeric amino acids, polymerized organic acids (such as poly(lactic-co-glycolic acid), exopolysaccharides, and the like. These coatings can be applied by, for example, dip or spray coating onto the substrate.

The substrate can include any characteristic useful for supporting mold growth. For example, the substrate can include one or more of a swab, mesh-like device attached to a shaft, and/or free-standing meshes or screens, sponge, and/or combinations thereof. In some embodiments, the substrate comprises a material selected from the group consisting of polyester, polyurethane, cotton, foam, rayon, polyether or any combination thereof. In some embodiments, the substrate can be coupled to a shaft that is useful for allowing a technician to remove the substrate from the growth medium. The shaft of the swab can include any suitable material, such as polypropylene, wood, plastic, metal or any combination thereof. In some embodiments, the substrate is adhered to the bottom of a tube containing the growth medium. The growth medium and sample can be poured off after sufficient contact time with the substrate.

After mold growth has been adequately promoted, the substrate can be removed from the growth medium and placed in a buffer solution to concentrate the mold in a smaller volume and remove it from the product matrix. It can be useful to remove the mold from the product matrix because the product matrix, in many samples, including PCP samples, often include extraneous materials that can interfere with accurate mold detection during the detection step (e.g., by contributing to background counts), increasing the chance for a false positive result. The material being tested will be continued to be referred to as the "sample" herein, although the product matrix has been removed.

The buffer solution can include phosphates and may include salt. The buffer solution is useful for the reactionary phase of the fluorescent dyes used in some embodiments of the invention, and helps promote the stability of the sample. The buffer solution can also contain a chemical fragmenting agent to fragment the mold hyphae, as discussed further below. The buffer solution can also contain an anti-foaming agent, such as antifoam A, and/or antifoam 204 or the like. This is useful to suppress the formation of foam during any physical agitation of the sample, such as during mechanical fragmenting as discussed further herein.

In some embodiments, the sample is fragmented. Such fragmentation can be useful when the sample is subjected to a detection step, as described further below. The fragmenting step can be any method of causing any mold present within the sample to fragment. For example, the fragmentation can include disassociation of mold hyphae into individual segments. In some embodiments, the fragmenting is promoted by a chemical fragmenting agent and/or a mechanical fragmentation step.

As mentioned above, a chemical fragmenting agent can be used to break the hyphal segments apart and into individual objects that can be detected, such as by exposing the hyphal segments to a solution containing a chemical fragmenting agent. In some embodiments, the chemical fragmenting agent includes one or more of the following: organic acids (including, but not limited to, organic alkyl and aryl acids such as hexanoic, benzoic, and/or lactic acid); inorganic acids (including, but not limited to, sulfuric acid, perchloric acid, hydrochloric acid, and/or methane sulfonic acid); inorganic bases (including, but not limited to, NaOH, KOH and/or other sources of hydroxide ion or high pH conditions); oxidizing agents (including, but not limited to, $H_2O_2$, hypochlorite, and/or nitric acid); cationic agents (including, but not limited to, CTAB, dodecyltrimethyl ammonium salts, quaternized pyridinium salts and the like); surfactants (including but not limited to, Tween-20, Triton X-100, PEG and the like); alcohols (including, but not limited to, ethanol, isopropanol and the like); and/or enzymes that attack cells walls (including, but not limited to, beta-glucanase, chitinase, protease, and/or cellulase). In some embodiments, the chemical fragmenting agent includes acetic acid. The chemical fragmenting agent can be included in a solution in any concentration range useful for fragmenting the mold in the sample. For example the chemical fragmenting agent can be in a concentration range of about 100 nM to about 5M (i.e., about 0.01% v/v to about 25% v/v). In some embodiments, the concentration is about 80 mM to about 4.16 M (i.e., about 0.5% v/v to about 25% v/v).

Also as mentioned above, some embodiments of the invention include a mechanical fragmentation step to fragment the sample. The mechanical fragmentation step can include any process useful for fragmenting the sample. In some embodiments, the mechanical fragmentation step includes sonic, high shear force, or other methods to disrupt the connections between the hyphae segments; mechanical agitation of a fluid containing the mold using any of a variety of devices (including, but not limited to, vortexers, shakers, mixers, magnetic stir bars, homogenizers, pulverizers and the like); mechanical agitation of the fluid containing the mold and also containing small bead-like objects that assist in disrupting the connections between the hyphae segments (including but not limited to, ceramic beads, stainless steel beads, glass beads, small mineral or other inorganic particles, such as metal oxides, and the like); exposure to sonic energy (including, but not limited to, sonic cell disruptors, probe sonicators, ultrasonic cleaning baths and the like); and/or forcing the fluid containing the mold through a small orifice at a high flow velocity so as to generate large shear forces in such a way as to cause disruption of the connections between the hyphae segments using any of a variety of apparatuses (including but not limited to, syringes, fluid jets, counter-rotating coaxial cylindrical chambers and the like). Any of these mechanical fragmentation steps can be performed in lieu of or in addition to utilization of any of the chemical fragmenting agents described above. Further, a solid article (e.g., small bead-like objects, metallic beads, ceramic beads, chips of ceramic materials, magnets, and the like) can also be utilized with any of these processes and/or devices to fragment the mold, such as by grinding or pulverizing the mold within and on the side of a sample tube.

In some embodiments, any solid article (e.g., substrate useful for growing mold) present is removed from the process before the mold is fragmented. For example, in some embodiments the mold is extracted from the solid article in the buffer solution. In other embodiments, the solid article is subjected to the fragmenting step and removed from the sample after the fragmenting step. In either embodiment, a portion of the solid article can be present in the mold detection step. For example, as mold grows enzymes are released that act to enhance the spread of mold (e.g., mold that grows on wood releases cellulase that breaks down cellulose in the wood grain). This allows the mold to attach and penetrate this substrate for growth. A similar phenomenon may also occur on the solid article, and when the sample is subjected to fragmentation these affected areas can 'shed' the solid article as well as the mold. In some embodiments, as discussed further below, the substrate is not removed from the sample before the detection step.

In some embodiments, the fragmented sample is labeled with a labeling agent. The labeling agent can be any agent capable of associating itself with any mold segments present in the sample which can be detected in a detection step. The labeling agent can be used as a proxy for detecting the presence or absence of the mold fragments in the detection step. Examples of labeling agents include fluorescent agents and luminescent agents which can be detected by fluorescence and luminescence, respectively.

In some embodiments, fluorophores are introduced to the sample, such as by fluorescent labeling of the hyphae segments, and the presence of the mold can be detected from these labeled segments using fluorescence. In other embodiments, a luminescent agent, such as luciferase or adenylate kinase, is introduced to the sample and the presence or absence of mold in the sample can be detected by adenosine triphosphate (ATP)-induced luminescence.

In certain embodiments, following fragmentation of the mold hyphae into smaller units, they are exposed to a fluorescent labeling agent. The fluorescent agent can include any agent useful for fluorescently labeling the sample. In some embodiments, the fluorescent agent includes nucleic acid dyes/stains, fluorochrome labeled anti-mold (component) antibodies, mold specific stains, and/or fluorochrome labeled nucleic acid probes. The fluorescent labeling agent may include nucleic acid dyes/stains ( including, but not limited to, Syto 62, Syto 61, Syto 59 (Invitrogen), Hexidium Iodide or the like); mold specific stains (including, but not limited to, Calcofluor white, Fluorescent Brightener 28 or the like); or fluorescent stains (including, but not limited to, trypan blue, aniline blue, congo red and the like); fluorochrome labeled antibodies or probes (fluorochromes, including, but not limited to, Cy5 (Amersham), Alexa 647 (Invitrogen), WellRed dyes, Oyster family dyes (the latter two available from IDT Technologies), Evoblue30 (Sigma) or the like). The stains/dyes generally stain external and internal mold components, the fluorochrome labeled antibodies generally target external distinctive epitopes unique to that mold strain, and the fluorochrome labeled probes generally target the DNA/RNA of the internal mold structure.

In some embodiments, the fluorescent agent includes immobilized fluorophores. Such immobilized fluorophores can be immobilized on a surface in contact with the samples, such as latex spheres, magnetized spheres, and nanoparticles.

In some embodiments, a quenching agent can be applied to the fluorescently labeled sample to block non-target labeling. Such a quenching agent is useful for the quenching of non-target segments. For example, Acid Black (e.g., Acid Black 48), Irgalon, Acid Blue or the like can be used as a quenching agent.

After association with fluorophore, the presence or absence of the mold can be detected by detection of the fluorophore. In some embodiments, detection of the individual fluorescently labeled segments is achieved using flow cytometry.

In some embodiments, a flow cytometer includes a housing and a sample inlet adapted to allow a sample to be injected into the flow cytometer. The flow cytometer also includes a light wave source (e.g., a laser source) for passing light through the sample. The flow cytometer also can include electronics for sensing, measuring, manipulating and reporting the fluorescence of the sample as it passes through the light source. Further, the flow cytometer can include electronics for sensing, measuring, manipulating, and reporting a light scattering signal produced as the sample is passed through the light source. An example of a flow cytometer useful for utilization with embodiments of the invention is the RBD 3000, produced by Advanced Analytical Technologies, Inc., assignee of the present application.

In embodiments utilizing a flow cytometer for detection of the mold, the sample is placed into the flow cytometer. Detection is achieved by measurement of the fluorescence and scattering signals that are generated as the hyphal fragments pass through a laser beam that intersects the sample path. The flow cytometry measurement can be triggered by either the fluorescence or scatter signal. Upon triggering, both measurements (fluorescence and scatter) can be captured by electronics. The population of mold hyphal fragments is identified by virtue of its location on the scatter plot. Because of its unique and reproducible position in the scatter plot, the mold fragments can be distinguished from other materials in the sample.

For example, the method can be performed on known negative product samples and analyzed on the flow cytometer. The output of the flow cytometer, such as an intensity plot, establishes a baseline for that particular product matrix. The negative samples have no hyphal fragments but may have background counts due to the product matrix. Once the baseline has been established, all test samples tested in this product matrix can be divided against the baseline to establish a signal to noise ratio. Signal to noise ratios greater than or equal to a predetermined multiple or ratio above the baseline can be considered positive in the mold presence/absence test. There may also be an ambiguous range that falls below the positive range and above the negative range. A positive to negative ratio that falls below the ambiguous range would be considered negative.

In some embodiments, the size of the hyphal fragments can also be determined. It may be useful to know the approximate size of the mold fragments to verify the test results with expected results, i.e. if mold fragments are very large they will present as counts with high scatter and high fluorescence. Various embodiments of the invention include several ways to measure the sizes of such fragments. These include use of static (normal) light scattering at a variety of angles such as in a flow cytometric measurement; use of dynamic light scattering in which Brownian motion of the particles affects the signal intensity and by which fragment size can be determined by the time dependence of the change in this signal; use of a Coulter counter type of device in which the fragments pass through a small orifice thereby affecting the electrical conductivity through the orifice; immobilization of the fragments at a surface and analysis using any of a variety of size dependent measurements such as scanning probe microscopies, interferometric (metrology-like) measurements and the like.

Further, fluorescence can be measured using fluorescent microscopy, in which the fluorescence characteristics of individual fragments are measured as the fragments pass through a laser beam. Alternatively, bulk fluorescence, in which the fluorescence from the labeled fragments is detected by a measurement on the entirety of the solution, can also be used to detect the presence of the mold. Another detection method includes an ultraviolet microscope, in which the mold fragments are associated with a labeling agent and detected by an operator using an ultraviolet scope.

In some embodiments, the method of the invention does not include a fragmentation step. In such embodiments, mold is left on a substrate used to support mold growth. The fluorescent labeling steps described above are then performed by exposing the substrate to a solution containing the labeling agent. Unwanted fluorescence can be quenched by exposing the substrate to a solution containing a quenching agent. The presence of mold can be detected by placing the entire substrate into a fluorescence chamber such that the presence of mold can be detected by the fluorescence of the label attached to the mold. In certain embodiments, the quenching agent may be added directly to the fluorescence chamber, as, for example, in the case in which the substrate is present in the chamber immersed in a solution containing the quencher.

Accordingly, embodiments of the invention include a method of detecting the presence or absence of mold in a sample that significantly reduce the time to detection compared to traditional tests. Further, embodiments of the invention include a medium for growing mold that contributes to the reduction of the time required before the mold can be detected.

EXAMPLES

The following examples are presented for illustrative purposes and are not intended to limit the scope of the claims that follow.

Generally, after product neutralization (i.e., the neutralization of any antimicrobial agents present in the product), the sample is placed in a growth medium that contains a swab. This medium stimulates hyphal growth in the mold life cycle to a detectable level within 24 hours and the swab provides a substrate for the mold to adhere to. The swab sample is then removed from the growth medium after 24 hours and placed in a buffer solution. The sample is then subjected to chemical additives and/or mechanical forces to shear the hyphal strands. The sample is diluted, stained with a fluorochrome, counterstained with a quenching agent and analyzed on a RBD 3000 flow cytometer. PCP materials containing mold contaminants have fluorescence and scatter signals that indicate a compromised material.

More specifically, the following example represents the difference between a positive mold sample (at a low spike number) and a negative sample, which is the same as the positive minus the mold spike. This example includes growth enhancement media only (i.e., there was no product tested in this example). The growth medium used was Tryptic Soy Broth at a concentration of 30 g/L; soy lecithin at a concentration of 5 g/L, Tween-20 at a concentration of 40 mL/L; malt extract at a concentration of about 10 g/L; and dextrose at a concentration of about 10 g/L. A swab was placed in 20 mL growth enhancement media in duplicate. Two samples, each in a separate tube, were prepared, and a mold spore spike was added to only one of the tubes. Both tubes were then placed at 30° C.±2° C. on an orbital shaker for incubation. After 24 hours, the samples were removed from the incubator, the swab removed from the tube and placed into a sterile 15 mL conical tube containing 2 mL of phosphate buffer. The tube was then subjected to a high vortex for 30 seconds and let sit 10 minutes for foam to settle. The sample was diluted 1:10 in filtered phosphate buffer and analyzed on a flow cytometer under a method that uses 2× nucleic acid dye as the labeling agent with 1× Acid Black as the quenching component.

As shown in FIG. 1, the signals generated from the labeled mold hyphae are shown in the boxed region of the plot of scatter signal versus fluorescence signal (a so-called scatter plot). The primary population of hyphal fragments is in the lower left region of the plot. Each point in this plot corresponds to a mold hyphae fragment passing through the laser beam in a flow cytometry measurement. The plot can be color coded to indicate the relative amount of particles present on a particular coordinate of the plot. The number of such points can be related to the presence of mold in the original sample. Test samples are considered positive when the signal to noise ratios of the boxed sample area meet or exceed a value determined by a product matrix or sample type.

Figure 2:
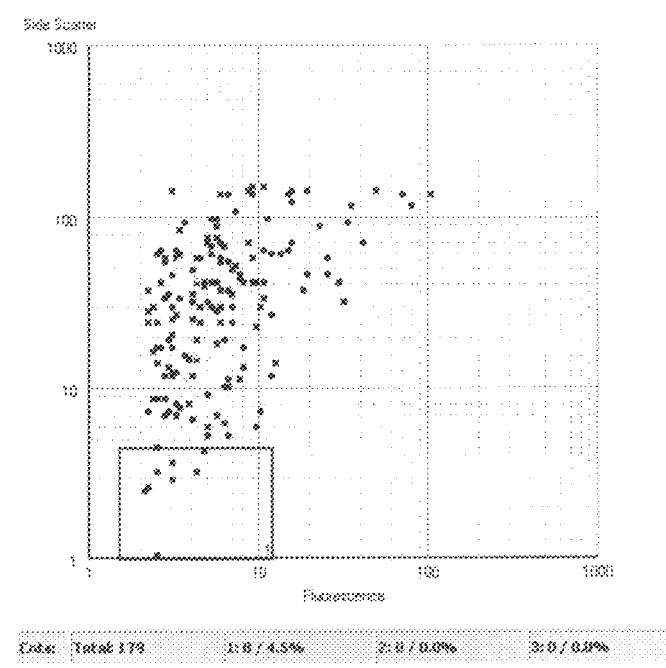
FIG. 2 shows a scatter plot of the growth medium of FIG. 1 without mold hyphae in accordance with an embodiment of the invention.

FIG. 1 shows the type of measurement used to detect mold in such an analysis. In the example shown in FIG. 1, the actual counts are represented in the intensity plot: Total=total counts on the intensity plot; 1=counts represented by box 1 on the intensity plot (a predefined area in this example)/ the percentage of counts in box 1 as compared to the total counts; 2=counts represented by box 2 on the intensity plot (this box was not predefined in this example)/ the percentage of counts in box 2 as compared to the total counts; 3=counts represented by box 3 on the intensity plot (this box was not predefined in this example)/the percentage of counts in box 3 as compared to the total counts. FIGS. 1 and 2 show a plot of scatter intensity (y axis) versus fluorescence intensity (x axis). FIG. 2 is an intensity plot that represents the identical sample without the mold. Accordingly, no, or very few, scattering fragments are in the predefined box 1 area of FIG. 2.

Also by way of example and not limitation, a representative test method is provided below:

1. 10 g of product to 90 mL of growth enhancement media (GEM).
2. Remove 1 mL of product mixture and place in 19 mL of growth enhancement media.
3. Place swab in 20 mL growth medium+sample and incubate at 30° C.±2° C., shaking overnight.
4. Remove swab after set time—usually 24 hours but can be sooner—and place in 2 mL of buffer solution.
5. Either vortex, sonicate, or add an oxidizing agent or any combination thereof.
6. Dilute sample 1:10 in buffer.
7. Analyze on the RBD using nucleic acid stain, Acid Black quencher.

Compare results to negative baseline. Anything greater than or equal to the predetermined positive cut off for the signal to noise ratio is considered positive.

While the invention has been described in conjunction with specific embodiments thereof, it is evident that many alternatives, modifications, and variations will be apparent to those skilled in the art in light of the foregoing description. Accordingly, it is intended to embrace all such alternatives, modifications, and variations, which fall within the spirit and broad scope of the invention.

What is claimed is:

1. A method of detecting the presence or absence of a mold having hyphae, comprising:
   (a) applying a sample suspected of containing the mold to a volume of liquid growth medium containing a porous substrate attached to a shaft, wherein said porous substrate attached to a shaft is not used to collect the sample prior to step a);
   (b) allowing growth of said mold to occur in said liquid growth medium of step a) and for said mold to attach onto said porous substrate attached to a shaft;
   (c) transferring said mold attached to said porous substrate attached to a shaft from step b) to a phosphate buffer solution by:
      i) removing said porous substrate attached to a shaft with attached mold from said liquid growth medium; and
      ii) placing said porous substrate attached to a shaft with attached mold into a smaller volume of phosphate buffer solution, wherein said volume of phosphate buffer solution is less than the volume of liquid growth medium from which it was removed;
   d) mechanically fragmenting said mold in said volume of phosphate buffer solution from step c) by subjecting said porous substrate attached to a shaft with attached mold to a shear force to disrupt connections between segments of the hyphae and produce fragmented mold hyphae segments;
   e) associating said fragmented mold hyphae segments sample of step d) with a labeling agent; and
   f) directly detecting the presence or absence of said mold hyphae segments with said labeling agent of step e) by flow cytometry;
      wherein the liquid growth medium comprises a nitrogenous substance and a carbon source.

2. The method of claim 1, wherein the sample of step a) includes a personal care product.

3. The method of claim 1, wherein the sample of step a) includes an over-the-counter product.

4. The method of claim 1, wherein the labeling agent of steps e) and f) includes a fluorescent agent.

5. The method of claim 4, wherein the fluorescent agent is selected from the group consisting of nucleic acid dyes, nucleic acid stains, fluorochrome labeled anti-mold antibodies, mold specific stains, fluorochrome labeled nucleic acid probes, and combinations thereof.

6. The method of claim 4, further including the step of; adding a quenching agent after associating the sample with the fluorescent agent.

7. The method of claim 1, wherein the liquid growth media further comprises a stimulation agent including n-acetyl glucosamine.

8. The method of claim 1, wherein said shear force is comprised of mixing, vortexing or sonication.

* * * * *